United States Patent
O'Connor et al.

(10) Patent No.: US 10,566,093 B2
(45) Date of Patent: Feb. 18, 2020

(54) DATA INTEGRATION USING GRAPH STRUCTURES

(71) Applicant: C/HCA, Inc., Nashville, TN (US)

(72) Inventors: Niall O'Connor, Somerville, MA (US); Mickey Alan Correll, Cambridge, MA (US); Kathryn Hopkins McGill, Cambridge, MA (US); Luke Connors, Boston, MA (US); Daniel Schlauch, Lexington, MA (US)

(73) Assignee: C/HCA, Inc., Nashville, TN (US)

(*) Notice: Subject to any disclaimer, the term of this patent is extended or adjusted under 35 U.S.C. 154(b) by 0 days.

(21) Appl. No.: 16/298,748

(22) Filed: Mar. 11, 2019

(65) Prior Publication Data

US 2019/0286661 A1    Sep. 19, 2019

Related U.S. Application Data

(60) Provisional application No. 62/642,420, filed on Mar. 13, 2018.

(51) Int. Cl.
| | | |
|---|---|---|
| *G06F 17/30* | (2006.01) | |
| *G16H 50/20* | (2018.01) | |
| *G06N 20/00* | (2019.01) | |
| *G06F 16/901* | (2019.01) | |
| *G06K 9/62* | (2006.01) | |

(52) U.S. Cl.
CPC ......... *G16H 50/20* (2018.01); *G06F 16/9024* (2019.01); *G06K 9/6262* (2013.01); *G06N 20/00* (2019.01)

(58) Field of Classification Search
CPC ....................................................... G06F 16/00
See application file for complete search history.

(56) References Cited

U.S. PATENT DOCUMENTS

| | | |
|---|---|---|
| 6,317,700 B1 | 11/2001 | Bagne |
| 9,542,450 B1 | 1/2017 | Jacobsson |
| 9,632,654 B1 * | 4/2017 | Elassaad ............... G06F 16/951 |
| 2009/0058859 A1 | 3/2009 | Crawford |
| 2013/0151277 A1 | 6/2013 | Thiers |
| 2014/0336943 A1 | 11/2014 | Pellini |
| 2015/0046191 A1 * | 2/2015 | Futscher de Deus ....................... G06F 19/3456 705/3 |
| 2018/0052962 A1 | 2/2018 | Van Der Koijk |
| 2018/0075359 A1 | 3/2018 | Brennan |
| 2018/0137247 A1 | 5/2018 | Bore |
| 2019/0005395 A1 | 1/2019 | Dutkowski |

FOREIGN PATENT DOCUMENTS

WO    2011/077353 A2    6/2011

OTHER PUBLICATIONS

First Action Interview Pilot Program Pre-Interview Communication dated May 13, 2019 in related U.S. Appl. No. 16/298,541, 4 pgs.
(Continued)

*Primary Examiner* — Khanh B Pham
(74) *Attorney, Agent, or Firm* — Kilpatrick Townsend & Stockton LLP

(57) ABSTRACT

Methods and systems disclosed herein relate generally to using graph structures and parent-child node configurations to facilitate data integration across corresponding investigatory events.

20 Claims, 7 Drawing Sheets

(56) References Cited

OTHER PUBLICATIONS

First Action Interview Office Action Summary dated Jul. 23, 2019 in related U.S. Appl. No. 16/298,541, 5 pgs.
First Action Interview Pilot Program Pre-Interview Communication dated Jun. 13, 2019 in related U.S. Appl. No. 16/298,914, 14 pgs.
Extended European Search Report dated Jul. 2, 2019 in related foreign application No. 19162631.6, 76 pgs.
Isern D et al: 11 Computer-based execution of clinical guidelines: A review 11 International Journal of Medical, Informatics, Elsevier Scientific Publishers, Shannon, IR, vol. 77, No. 12, Dec. 1, 2008 (Dec. 1, 2008), pp. 787-808, XP025584756, ISSN: 1386-5056, DOI: 10.1016/J.IJMEDINF.2008.05.010.
First Action Interview Office Action Summary dated Aug. 19, 2019 in related U.S. Appl. No. 16/298,914, 20 pgs.

* cited by examiner

DATA INTEGRATION USING GRAPH STRUCTURES

CROSS-REFERENCE TO RELATED APPLICATIONS

This application claims the benefit of and the priority to U.S. Provisional Application No. 62/642,420, filed on Mar. 13, 2018, which is hereby incorporated by reference in its entirety for all purposes.

FIELD

Methods and systems disclosed herein relate generally to using graph structures and parent-child node configurations to facilitate data integration across related investigatory events.

BACKGROUND

Various approaches for potentially addressing specific conditions are very frequently evaluated using investigatory events. Unfortunately, frequently each event is performed and/or assessed in relative isolation. This is despite the fact that a given investigatory event very typically overlaps to some degree with one or more other investigatory event (e.g., in terms of a type of event or protocol being investigated, selection criteria, etc.). Not only does this approach then result in sub-optimal assessment of results of the events, but it also hinders the potential for identifying and implementing design improvements for subsequent investigatory events.

A challenge with improving data integration is addressing a very high degree of variability of event protocols, selection techniques and semantic coding across the events. This variability results in challenges in even identifying similarities across events, much less aggregating data in a sound manner.

SUMMARY

In some embodiments, a computer-implemented method is provided. A graph model can be availed. The graph model can include a graph structure that connects a set of nodes and a set of edges. Each edge of the set of edges can connect two nodes. The set of nodes can include a plurality of end nodes. Each end node of the plurality of end nodes can identify an investigatory event. For each entity of a set of entities, a set of operations can be performed. The set of operations can include identifying a starting node from amongst the set of nodes based on first electronic data associated with the entity and generating one or more graph-structure trajectories through part of the graph structure based on second electronic data associated with the entity. Each graph-structure trajectory of the one or more graph-structure trajectories can extend from the starting node through one or more edges and can connect to one or more other nodes of the set of nodes. Generating the one or more graph-structure trajectories can include iteratively determining, for each graph-structure trajectory of the one or more trajectories, whether to extend the graph-structure trajectory to a next node in a path based on at least part of the second electronic data and a criteria group of the next node until the graph-structure trajectory terminates. The set of operations can further include storing graph-structure trajectory data characterizing each of the one or more graph-structure trajectories in association with an identifier of the entity. A parent node can be identified that is connected to a plurality of child nodes via a corresponding edge. Each of the plurality of child nodes can be associated with a corresponding investigatory-event specification that is more specific than an investigatory-event specification associated with the parent node. A subset of the set of entities can be identified based on the stored graph-structure trajectory data. Graph-model trajectory data for each entity in the subset can indicate that a graph-structure trajectory associated with the entity connected to a child node of the plurality of child nodes. Investigatory-event data can be retrieved that is associated with the subset of the set of entities. A data integration result can be generated based on the investigatory-event data. The data-integration result can be generated to correspond with the investigatory-event specification associated with the parent node. The data-integration result can be output.

In some embodiments, a system is provided that includes one or more data processors and a non-transitory computer readable storage medium containing instructions which when executed on the one or more data processors, cause the one or more data processors to perform part or all of one or more methods disclosed herein. In some embodiments, a computer-program product is provided that is tangibly embodied in a non-transitory machine-readable storage medium, including instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

Figure 1A:
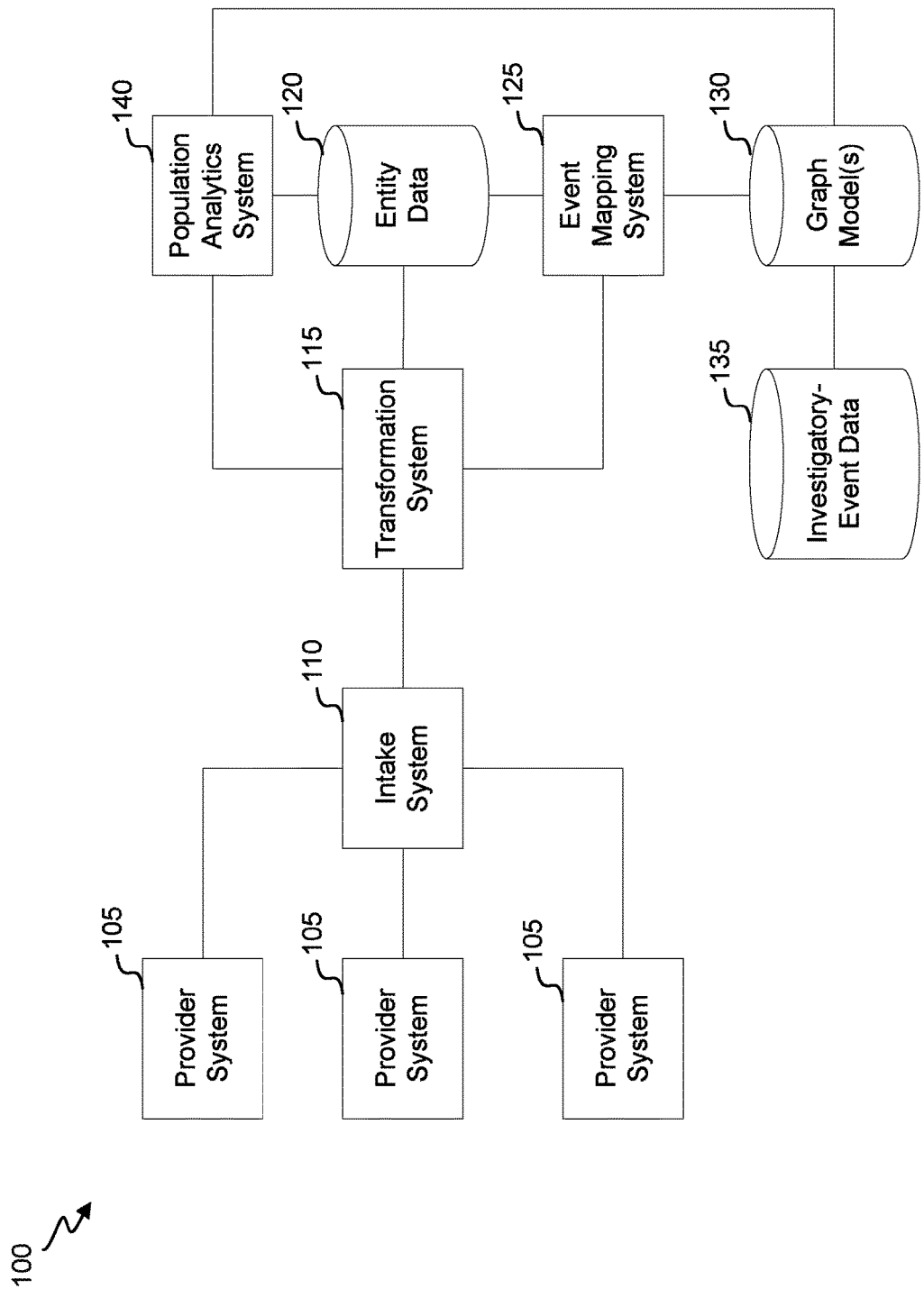
FIG. 1A depicts an exemplary interaction system for processing entity data to generate investigatory-event mappings and population-analytics results.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

In some instances, techniques are provided for facilitating data integration across investigatory events using a graph model. Specifically, a graph model can include a graph structure that includes a set of connected nodes. A subset of the set of connected nodes include a plurality of end nodes—each of which corresponds to an investigatory event. With respect to each end node, a path (that includes multiple edges) is defined that connects a starting node (identified for the investigatory event) to multiple intermediate nodes and finally to the end node. Each node can correspond to a criteria group (that includes a single criterion or multiple criteria) that serves as an inclusion criteria group or an exclusion criteria group. Each criteria group can be configured to evaluate one or more particular types of entity data to determine whether a specified constraint is satisfied. For example, a given starting node may correspond to an inclusion criteria group that indicates that entity data corresponding to an entity must identify a particular condition in order to advance a trajectory from the starting node towards the end node for the entity.

A general rule, node-specific rule or investigatory-event-specific rule can indicate how a trajectory is to be effected in instances in which a type of entity that is to be processed is absent from an entity data set. For example, in some instances, the rule may indicate that this is to result in termination of the trajectory if a presently evaluated criteria group is an inclusion criteria group or for all criteria groups; that a trajectory is to be extended to evaluate a criteria node of a next node (e.g., while potentially decreasing a score or confidence associated with the present node for the entity), or that a request for the missing data is to be transmitted or presented. In addition to mapping investigatory events with events via trajectory length, node-specific evaluation results may be used to score a given mapping to facilitate ranking some completed trajectories above others. A node-specific evaluation result may indicate (for example) an extent to which an entity-specific data point corresponds to a target data point specified in the criteria group, whether a logic condition of the criteria group was satisfied based on the entity data, whether (or an extent to which) a particular type of data to be evaluated in the criteria group was present in an entity data set, and/or a confidence of entity data evaluated by the criteria group.

The graph structure can thus be configured to represent criteria for many investigatory events. Use of the graph structure can thus generate trajectories that indicate (for example) each investigatory event (represented in the graph structure) for which a given entity is or may be eligible and further each entity (represented via trajectory data) that is or may be eligible for a given investigatory event.

Each investigatory event may be defined based on one or more specifications. In some instances, an investigatory event is a clinical trial and the one or more specifications identify (for example) a characteristic of a treatment to be administered (e.g., an identification of a drug, dosing scheme, administration protocol, medical-device therapy, etc.) and/or a definition of a patient group to be accepted into the trial. In some instances, a specification of the one or more specifications corresponds to a criteria group associated with investigatory event. For example, a specification can identify a condition (e.g., disease) of entities to be accepted to the investigatory event.

Various techniques may be used to identify each of one, more or all specifications that correspond to an investigatory event. For example, each investigatory event may be associated with a path that extends from a starting node to an end node. The path can traverse individual elements (e.g., nodes and potentially edges) that are associated with individual criteria groups. Thus, the graph structure can associate an individual investigatory event with a set of criteria groups. A specification can be identified as a constraint as specified in a criteria group. As another example, metadata can be received and stored in association with an identifier of an investigatory event, where the metadata identifies a specification of the investigatory event. For example, the metadata may characterize the particular type of event. Thus, a specification can be identified by querying a (e.g., remote or local) data structure with an identifier of the investigatory event.

The specifications can be used to facilitate data integration. Specifically, multiple investigatory events that correspond to a same or similar specification may be identified. The identification may be facilitated by the graph structure. For example, detecting that each of multiple investigatory events have a path that intersects a same node can indicate that the multiple investigatory events share a specification that corresponds to a criteria group of the node. The same node can thus be identified as a parent node from which event-specific paths extend in different manners to intersect different subsequent "child" nodes (e.g., immediately after the parent node or after multiple nodes), with the different child nodes representing event-distinguishing data.

As another example, a particular specification can be identified (e.g., via user input, in response to detecting the particular specification in relation to a new investigatory event or as a result of iteratively evaluating some or all specifications represented in graph-related data). The graph structure and/or event-related metadata can be queried to identify each investigatory event associated with the particular specification. A parent node may be identified as a lowest-level node (e.g., closest to end nodes) from which paths corresponding to the identified investigatory event all intersect. Alternatively or additionally (e.g., and potentially selectively in instances in which no such parent node is identified or no such parent node that is not of at least a designated distance from an end-node layer), a new parent node may be generated. A constraint group for the new parent node may indicate that entity data is to correspond to the specification. Edges may be generated to connect the new parent node to "child" nodes corresponding to paths of the investigatory events identified in the query result.

In some instances, data is to be integrated across investigatory events that relate to one or more same specifications. In some instances, data is to be integrated across investigatory events that related to one or more similar specifications. The similar specifications may include (for example) different specifications that are of a same type (e.g., that correspond to a same type of disease, same class of drug, etc.). A data structure or input can identify a set of first specifications being more narrow versions of a second specification, such that data from investigatory events corresponding to each of the set of first specifications (e.g., and potentially also from any investigatory event corresponding to the second specification) can be integrated. To illustrate, a set of first specifications may identify particular types of eye disorders, while the second specification may represent the general class of eye disorders. A graph structure may represent this relationship between the first specifications and second specification (e.g., by having a parent node that corresponds to a general "eye-disorder" criteria group and that branches into multiple second child nodes that correspond to specific-disorder criteria group) or may not (e.g., by not including the parent node or by not having edges that connect a node corresponding to a general "eye-disorder" criteria group to disorder-specific nodes). In instances in which no parent node exists, one may be generated and connected to each "child" node representing more specific and/or more narrow criteria groups. Investigatory-event paths that traverse a child node may be extended to further traverse the parent node. Data can then be aggregated across investigatory events represented via end nodes associated with paths that traverse the parent node.

In some instances, specifications corresponding to two or more investigatory events are formatted differently, use a different vocabulary, use a different syntax and/or have a different structure. Thus, a mapping may be identified to determine an extent to which and/or whether different specifications correspond to a same (e.g., or similar) meaning. For example, a first investigatory event may specify criteria groups and/or event parameters (e.g., specifications of interventions to be used in the event) using the Medical Subject Headings (MeSH) vocabulary, while a second investigatory event may specify criteria groups and/or event parameters using an International Classification of Diseases (ICD) codes. Mappings between the two vocabularies may be identified using a look-up table, received via user input and/or learned. Nodes that include criteria groups that use the different vocabularies (or syntax, structures or formats) can then be designated as child nodes and connected to a parent node that represents the underlying shared meaning.

Identifying multiple investigatory events that correspond to a same or similar specification can facilitate integrating data that characterizes one or more results of the multiple investigatory events and/or that characterizes entity assessments for the multiple investigatory events. For example, the one or more results may indicate an efficacy of a type of treatment (e.g., corresponding to a first shared specification) in treating a type of disease (e.g., corresponding to a second shared specification) and/or the prevalence of one, more or all adverse effects during the event. The one or more results can include (for example) a statistic, relationship, distribution or part or all of a model. For example, the one or more results may include a set of coefficients or a set of weights that correspond to a set of entity attributes and that indicate an extent to which a corresponding attribute was predictive of and/or correlated with a treatment outcome. The one or more results can then be aggregated (e.g., by performing a weighted average, generating a new set of weights or coefficients, etc.) to generate a meta-analysis result that is representative of a larger data set (e.g., and potentially reflective of a more diverse entity set).

As another example, the one or more results may indicate one or more attributes of entities selected for the investigatory events, one or more attributes of entities that declined participation in the investigatory events, one or more attributes of entities that were matched to the investigatory events but not selected. This aggregated information can be used to (for example) predict a time that will be required to successfully enroll a threshold number of entities in a new investigatory event having particular (same or related) specifications.

It will be appreciated that an investigatory event can include (for example) a clinical trial pertaining to a single a discrete event (e.g., a one-time treatment or surgery); an extended-duration event (e.g., administration of a multi-week therapy, or administration a week-long and continuous administration of stimulation via a medical device during which a magnitude is adjusted in accordance with a particular stimulation pattern; a multi-month time period during which a particular drug is taken in accordance with a dosing regimen); and/or multiple discrete events (e.g., multiple discrete administrations of a particular therapy; multiple doses of a drug to be taken in a prescribed manner; and/or multiple activations of a medical device to operate in a specific manner). The investigatory event can be defined to relate to a particular hypothesis, to define one or more defined endpoints, and to clearly identify one or more measurables to be collected at the endpoint(s). In some instances, the investigatory event includes and/or corresponds to a particular care-pathway evaluation, which can (for example) identify an order in which different treatments are to be administered, a manner and/or frequency in which a vital sign is to be measured (e.g., taking a blood-pressure measurement on a person's calf instead of arm), etc. The evaluation can be configured (for example) to compare a particular care pathway to another particular pathway or default (e.g., normal) data.

Further details pertaining to graph structures are disclosed in U.S. application Ser. No. 16/298,541, filed on Mar. 11, 2019 and entitled "TECHNIQUES FOR GENERATING INVESTIGATORY-EVENT MAPPINGS USING GRAPH-STRUCTURE TRAJECTORIES" and in U.S. application Ser. No. 16/298,914, filed on Mar. 11, 2019 and entitled "TECHNIQUES FOR INTEGRATING PROXY NODES INTO GRAPH-MODEL-BASED INVESTIGATORY-EVENT MAPPINGS." Each of these applications is hereby incorporated by reference in its entirety for all purposes.

FIG. 1A depicts an interaction system 100 for processing entity data to generate investigatory-event mappings and population-analytics results. A provider system 105 can be associated with a medical care provider (e.g., physicians, nurses, pharmacists, physician offices, hospitals, and/or laboratories). In response to receiving input and/or test result at a given provider system 105, the provider system 105 can transmit electronic data to an intake system 110. The electronic data can identify an entity (e.g., by name, social security number or other identifier). The electronic data can further identify (for example) a diagnosis, test result (e.g., result of a blood, urine, genetic or imaging test), prescription, and/or one or more symptoms. Intake system 110 may parse the electronic data to identify discrete field values and avail the values (in association with the entity identifier) to a transformation system 115. Transformation system 115 can translate codes into attributes, each having a standardized form. It will be appreciated that, in some instances, for at least one field value, no transformation is necessary to accord with the standardized form, such that a corresponding attribute is defined to be the attribute.

The standardized attributes can then be stored in an entity data store 120. The standardized attributes can further be availed to an event mapping system 125. Event mapping system 125 may use entity attributes for an individual entity to generate one or more trajectories throughout a graph model (stored in a graph model data store 130). The graph model can be managed to include criteria associated with open investigatory events, which can be determined using investigatory-event data from an investigatory-event data store 135 (e.g., which may be generated based on similarly processing communications from an investigator or investigatory-event data store to parse and transform information). The graph model and entity data may be stored to rely upon a same set of standardized data fields as fields corresponding to the standardized attributes, such that entity data corresponding to graph-model criteria can be easily identified. When a trajectory ends at an end node corresponding with an investigatory event, event mapping system 125 can transmit data to an entity device or provider system 105 that indicates that the entity is eligible for the investigatory event (e.g., and/or identifies each of multiple investigatory events for which the entity qualifies).

The standardized parameter data can further be availed to a population analytics system 140. Population analytics system 140 may identify (for example) a quantity and/or characteristics of entities that are eligible for particular investigatory events. Population analytics system 140 may characterize sub-populations of various groups (e.g., indicating percentages of a condition-specific entity group that corresponds to various age groups). Population analytics system 140 may further or alternatively use current and past entity data to predict a time period over which, cumulatively, a predefined number of eligible entities for a particular investigatory event will be identified (e.g., in view of the event's criteria). The prediction may further be used to predict a time period during which, cumulatively, a predefined number of entities will enroll in the particular investigatory event.

Event mapping (e.g., performed by event mapping system 125) can begin by identifying a starting node in the graph model based on entity data associated with the entity. For example, one or more starting nodes may be identified for the entity based on data (e.g., entity attributes) associated with the entity in an entity data store. The one or more starting nodes may correspond to (for example) a disease diagnosis or a symptom occurrence and/or one or more other factors (e.g., procedure history, demographic characteristic, family history, genetic-mutation characteristic, etc.). Each rule of the set of applicable rules can include criteria represented by a node and/or edge connected to a starting node of the one or more Edges and nodes connected to the starting node can be evaluated to determine whether the entity matches a corresponding particular inclusion criterion, avoids a corresponding particular exclusion criterion and/or meets a given combination of multiple criteria as defined by logical operator. Each criterion can relate to one or more entity attributes. Entity attributes can be extracts from, identified within and/or determined based on one or more medical records associated with the entity and/or inputs from the entity, a medical care provider or pharmacist. When the criterion is appropriately satisfied (e.g., inclusion criterion is met, exclusion criterion is avoided and/or a logic-operator-defined combination is satisfied) with respect to a given neighboring edge and connected node, a trajectory is initiated that extends to the connected node (extending from the starting node to the connected node). For each initiated trajectory, subsequent edges and nodes are iteratively evaluated to determine whether (and/or how) the trajectory is to extend (and/or branch apart) or whether the trajectory is to terminate.

Each of a set of end nodes represented in the graph model can correspond to a particular investigatory event. Each branch (one or more connected edges and nodes) extending from an end node can represent a criterion for the investigatory event. Thus, for a given entity, one or more starting nodes can be identified based on entity data (e.g., indicating a current condition). With respect to each starting node of the one or more starting nodes, the starting node may be positioned along or an endpoint of one or more investigatory-event-associated branches. For each branch, criteria represented along the branch can be iteratively (e.g., and conditionally) evaluated to determine whether the criteria is satisfied. For each branch extending from an investigatory-event node, a result can be determined for an entity that indicates (for example) one of: that the criteria/criterion of the branch is satisfied, that the criteria/criterion of the branch is not satisfied, an estimate that a criteria/criterion of the branch is satisfied, an estimate that a criteria/criterion of the branch is not satisfied, an estimated probability that a criteria/criterion of the branch is satisfied, an extent to which a criteria/criterion of the branch is satisfied or that the criteria/criterion of the branch was not completely evaluated due to a lack of pertinent entity data points. In some instances, an evaluation of a criteria can be performed to differentiate between instances in which a criterion is determined to be not satisfied based on the appropriate data and instances in which a criterion cannot be evaluated due to an unavailability of at least some data to be assessed using the criterion. For example, a weight associated with a node may be set to 0 if it cannot be assessed due to a lack of available or data but may be set to a negative value if data is available to assess the criterion and it is determined that the criterion is not satisfied. As another example, a weight associated with a node may be correlated with a resolution and/or confidence of data available and being used to assess a criterion.

The criteria evaluation may be conditional in that (for example) whether a trajectory extends to a given node in a branch for a given entity may depend on past results. For example, if a criteria/criterion associated with an earlier node is not satisfied, is not satisfied to a sufficient extent and/or is associated with a below-threshold probability of being satisfied, the trajectory may terminate such that criteria of subsequent nodes of the branch need not and/or will not be assessed for the entity. A score associated with the particular investigatory event and particular entity can be generated based on the results of the criteria assessment. The score may further depend on weighting of various branches. For example, a weight may be determined based on whether satisfaction of an inclusion criterion or clearing of an exclusion criterion is required. As another example, a weight may be determined based on a portion of the population (or a particular type of population) for which the criterion/criteria is satisfied. Investigatory events of potential interest for a given entity may be determined based on the score. For example, an identification of and/or information for each investigatory event associated with a score above a predefined threshold may be transmitted.

In some instances, a graph structure can be used to identify entities for a potential or actual synthetic control arm of an investigatory event. Specifically, the entities can be identified as each entity within a set of entities (e.g., for which a particular type of data is available and/or for which graph-model trajectories were generated within a predefined time period) for which each criteria of the investigatory event is satisfied and an additional constraint is satisfied or for which each criteria of the investigatory event except one or more specific criteria are satisfied. For example, the additional constraint may indicate that the entity has received or is assigned to an investigatory event to receive one of one or more predefined (e.g., standard-of-care) types of treatments. As another example, the one or more specific criteria may be configured to be satisfied when data indicates that the entity is not on a current standard-of-care treatment.

Figure 1B:
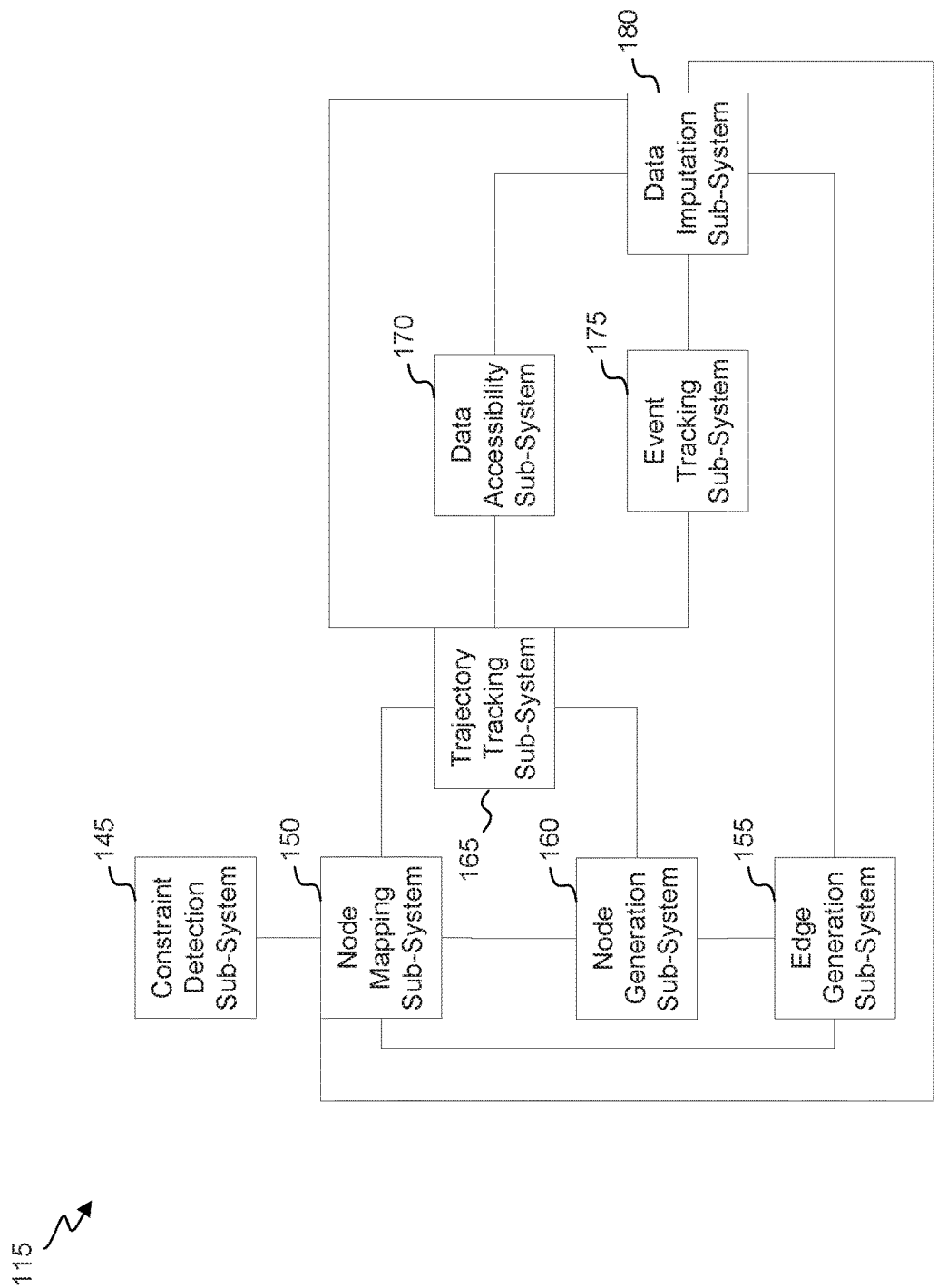
FIG. 1B depicts an exemplary transformation system for transforming electronic data into entity attributes.

FIG. 1B depicts an exemplary transformation system 115 for transforming electronic data into entity attributes. In some instances, part or all of the transformation system depicted in FIG. 1B and/or described in association thereof can be integrated into interaction system 100 depicted in FIG. 1A. Transformation system 115 can include a constraint detection sub-system 145 that detects a constraint associated with a new or newly modified investigatory event. The constraint may be included in a criteria group specified for the event. The constraint may be identified (for example) from input received over a network and/or via an interface and/or data included in a file (e.g., uploaded file) or electronic transmission. The constraint may relate to one or more entity attributes. The constraint may indicate that a condition is satisfied when (for example) a given attribute is set to a specified value; a given attribute is detected in entity data and/or a given attribute is within a specified open or closed range.

A node mapping sub-system 150 can perform a targeted or general query pertaining to a graph model to determine whether the graph model includes a node having a criteria-group constraint corresponding to the detected constraint. In some instances, node mapping sub-system 150 determines that a criteria-group constraint of an existing node corresponds to the detected constraint if, and only if, the condition constraint is an exact match to the detected constraint. In some instances, node mapping sub-system 150 determines that a criteria-group constraint of an existing node corresponds to the detected constraint if the constraints overlap (e.g., by at least a threshold amount). For example, the constraints may be mapped when (e.g., and only when) a range or specified-value list of the criteria-group constraint includes at least a designated fraction (or all) of a range or specified-value list of the detected constraint. As another example, the constraints may be mapped when (e.g., and only when) a range or specified-value list of the detected constraint includes at least a designated fraction (or all) of a range or specified-value list of the criteria-group constraint.

In instances in which a corresponding node is identified for a detected constraint, the corresponding node can be included in a path corresponding to the (e.g., new or modified) investigatory event. For example, metadata can be associated with the node that associates the node with an identifier of the investigatory event. Further, an edge generation sub-system 155 can generate one or more edges to connect the corresponding node to other (new or existing) nodes in the path corresponding to other constraints pertaining to the investigatory event.

In instances in which a corresponding node is not identified for a detected constraint, a node generation sub-system 160 can generate a new node that corresponds with a criteria group including the detected constraint. Further edge generation sub-system 155 can generate a plurality of edges, each of which can be configured such that one end of the edge connects to the new node and another end of the edge connects to another node (e.g., another new node or an existing node in the graph model). In some instances, node generation sub-system 160 generates multiple new nodes to represent the detected constraint, and edge generation sub-system 155 can generate a plurality of nodes to integrate the multiple new nodes into the graph model. For example, a constraint may indicate that a criteria group is satisfied when a given attribute is equal to any of three specified values. In some instances, this constraint may be represented by a single node. In some instances, this constraint may be represented by four nodes: three nodes that represent each of the three specified values and a fourth "OR" node.

Transformation system 115 can further be configured to configure graph models and constraint integration based on empirical and/or predicted availability of various types of data. For example, if a constraint relates to a type of entity attribute that is rarely (or never) included in entity data sets, is subjective, is a high-order descriptor and/or is difficult (or impossible) to detect, integration of a representation of the constraint may be performed to account for these practicalities. One illustration of a high-order descriptor is that an entity is of normal weight.

For example, transformation system 115 can include a trajectory tracking sub-system 165 that tracks trajectory data in association with particular nodes (e.g., a new node or a node to which a constraint is mapped). The trajectory data may indicate (for example) a number or fraction of trajectories that terminated at the node. This assessment may specifically indicate a number or fraction of entity representations for which a criteria group of the node was determined not to be satisfied. For example, if a criteria group of a node indicates that an age of an entity is to be between 18 and 65, the number or fraction may indicate a number or fraction of instances for which this criterion was evaluated using entity-specific data and was determined to be satisfied. The trajectory data may be determined (for example) by querying a trajectory data structure, querying a node-centric data structure, query an edge-centric data structure, and/or assessing one or more densities of trajectories (e.g., at a position closer to a starting node and at a position at or extending from the evaluated node).

In some instances, prior assessments and/or trajectories can provide criteria-group information that extends beyond a binary analysis. For example, the information may indicate whether entity data to be evaluated by the criteria group was available and/or a confidence of this data. A data accessibility sub-system 170 may determine this information by (for example) querying an existing entity data set and/or querying one or more other data structures or data sources for one or more particular types of data in association with the entity. Data accessibility sub-system 170 may identify a confidence of data based on (for example) a date on which the entity data to be evaluated by the criteria group was initially declared or defined, a system that initially declared or defined the entity data to be evaluated, a degree to which a field corresponding to the entity data to be evaluated matches a type of data as specified in the criteria group, etc. For example, if a criteria group relates to a stage of a disease, data accessibility sub-system 170 may identify a confidence metric associated with this type of data as being low if entity data identifying a stage is more than a predefined threshold time period old.

A rule (e.g., pertaining to a graph model in its entirety, pertaining to a specific node and/or pertaining to a specific investigatory event) may specify an effect that data unavailability or sub-optimal data confidence is to have on a trajectory. For example, a rule may indicate that a trajectory is to terminate or that a trajectory is to connect to the node (e.g., potentially while storing an indication of the data unavailability or decreased data confidence). In some instances, a trajectory is to extend across all paths connected to a starting node associated with an entity, but criteria-group results are to be stored and then aggregated across the path in a particular manner to determine whether individual investigatory events are matches for the entity.

Transformation system 115 can further include an event tracking sub-system 175, which can identify—for each end node (and thus for each investigatory event)—the entities accepted for the investigatory event. For example, user input may be locally received or detected via a communication transmitted by a user device. The user input may include a list of entity identifiers selected for the event and/or may indicate, for each of a set of entities, whether the entity was selected for the event.

A data imputation sub-system 180 can process the event-tracking data and trajectory data to impute or to infer a particular type of entity data (e.g., a meta-variable) and/or an evaluation of a particular criteria group based on one or more other types of entity data and/or one or more other evaluations of one or more other criteria groups. The imputation or inference may be performed (for example) for entity-data types that are unavailable or associated with a low confidence at least a predefined threshold number or percentage of times. In some instances, a general determination is made as to which types of data for which an imputation is to be performed. In some instances, an imputation is performed on an entity-specific basis (e.g., such that an imputation is performed or used in response to detecting that a particular type of entity data is unavailable or associated with a low data-confidence metric).

In some instances, in order to determine which types of data to use for the imputation and/or how to use the data for the imputation, data imputation sub-system 180 may (for example) fit a regression model, train a machine-learning model or perform a correlation to determine an extent to which entity data types (e.g., that are frequently available, frequently associated with high data confidence, available for a particular entity being assess and/or associated with high data confidence for a particular entity being assessed) are predictive of whether the entity will be selected for an investigatory event (or are predictive across an entity population of the data type being imputed or a result of a criteria-group assessment relating to the data type being imputed). For example, data imputation sub-system 180 may determine that a time since diagnosis and an initial disease stage identified at diagnosis can be used to impute a current disease stage.

In some instances, data imputation sub-system 180 can assess trajectories that intersect individual nodes to update each of one, more or all nodes in a graph model to be associated with a (e.g., new or updated) probability that reflects a likelihood that (for example) satisfaction of a criteria group associated with the node is predictive of one or both of: reaching an end node that terminates a path along which the node is positioned and being selected for an investigatory event associated with an end node that terminates a path along which the node is positioned. Further or additionally, data imputation sub-system 180 can assess trajectories that extend along paths that intersect individual nodes to update each of one, more or all nodes in a graph model to be associated with a (e.g., new or updated) probability that reflects a likelihood that (for example) one or more attribute-value characterizations and/or one or more results of assessment of criteria group(s) of one or more nodes positioned closer to a starting node along a path is predictive of a result of an evaluation of a criteria group of the node. Thus, the graph model may be a probabilistic graph model. These probabilities may be used to (for example) impute entity-data values in response to missing data, determine whether to accept entity-data values when they are associated with low confidence metrics and/or assign a weight to a result of a criteria-group evaluation for the node.

In some instances, an imputation can trigger a change or addition to a graph model. For example, a node that corresponds to the constraint group for which data is being imputed can be mapped to one or more other nodes that relate to criteria groups for which assessments are used for the imputation. As another example, metadata corresponding to the node that corresponds to the constraint group for which data is being imputed can identify how other entity data can be used to estimate the entity data to be assessed at the node (e.g., when the entity data is unavailable and/or is associated with low confidence and/or all of the time).

Figure 2:
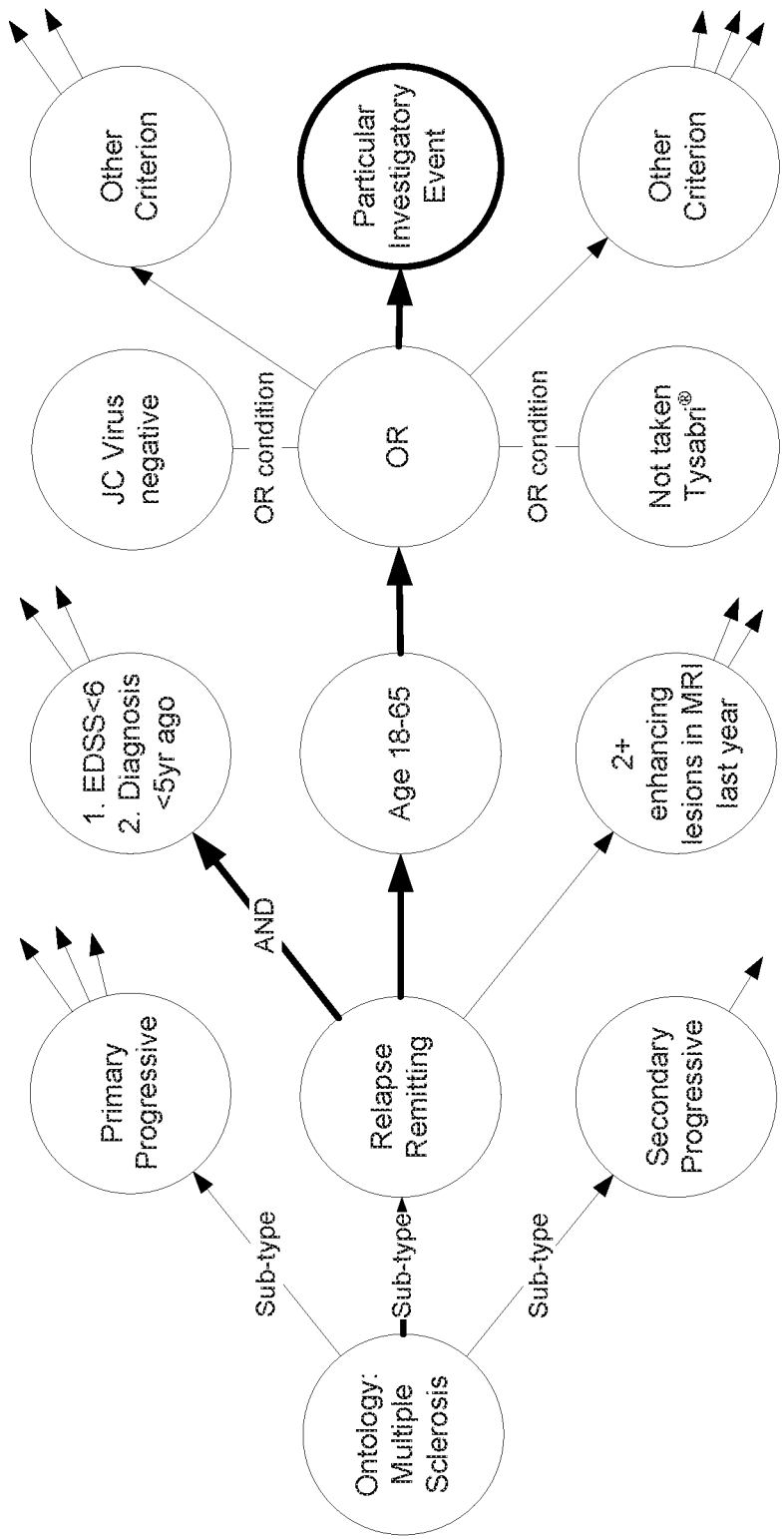
FIG. 2 shows an example of a portion of a graph model and trajectories associated with a given entity's data record.

FIG. 2 shows an example of a portion of a graph model and trajectories associated with a given entity's data record. In this instance, the entity's data record indicates that the entity has an autoimmune disease, such that the "Ontology: Autoimmune Nervous System Disorder" is identified as a starting node. In this example, the entity's data record does not explicitly identify a type of the autoimmune nervous system disorder, such that specific data is not available to assess the "Ontology: Multiple Sclerosis" node. The trajectory assessment can store an indication of the missing data but proceed along the trajectory.

Further, the entity's data record indicates that a disease stage is "Relapse Remitting", such that the Relapse-Remitting sub-type node is also identified as a starting node. This particular coded stage can be coded as a type of multiple sclerosis. Thus, even though the entity's data record does not specifically indicate that the entity has multiple sclerosis, the graph's indication that multiple sclerosis is a super-type of the relapse-remitting type supports a high-confidence estimate that the entity has multiple sclerosis, which can then also (or alternatively) serve as a starting node.

Identifying a starting node for an entity can include (for example) comparing condition-identifying data associated with the entity to each of a set of condition-identifying nodes in the graph model. In some instances, a given node may include multiple names (e.g., and one or more abbreviations) that may be used to refer to a same condition. Thus, the criterion associated with the node may be that data indicating an entity-specific condition matches (or matches to at least a predetermined degree) a condition identifier associated with the node.

In some instances, a particular criterion can be grouped with one or more other criteria for collective evaluation of the criteria within the group. Various criteria within the group may, but need not, relate to different types of field values and/or entity-data types relative to each other. In some instances, a criteria group includes only a single criterion (e.g., if a given criterion is not to be collectively evaluated with one or more other criteria).

A criteria-group score may be assigned to the criteria group that relates to an estimation as to whether a given criteria group is satisfied with respect to a particular entity. The score may be based on whether and/or a degree to which entity data matches or otherwise accords with (e.g., is within a designated range) the relapse-remitting criterion and/or a confidence in estimating that a criteria-evaluation result is accurate. For example, a given criteria group may indicate an entity is to be between 24 and 55 years old. An entity's age may be available in entity data, such that this criterion can be assessed to produce a binary result. However, if a birth date is not present and/or an indication as to when the age data was provided, a confidence may be less than 100%. A score may then be generated to be a sub-optimal result. As another example using the same criterion, entity data may lack information indicating an age of an entity, but an age may be estimated (e.g., based on a listed profession, health metrics, etc.). A confidence of the age may be generated based on the data fields used to generate the estimate, a consistency as to which age brackets various data-field values correspond, etc. The score can then be generated based on the estimate and confidence.

In some instances, a score may further or alternatively indicate an extent to which entity data indicates that the entity is eligible for the investigatory event. Thus, even if criteria groups for multiple groups are all clearly satisfied with high certainly, the criteria groups may be assigned different scores. For example, a score may depend on population data indicating how frequently the criteria group (or a part of the criteria group) is satisfied. When few entities satisfy the criteria, yet the entity is amongst the few, the score may be higher relative to criteria commonly satisfied. The criteria-group score may further or alternatively be based on a weight assigned to the criteria (or a part of the criteria) by a user associated with the investigatory event.

In some instances, rather than included multiple criteria in a single node, whether a trajectory extends in a given direction may depend on criteria assessments performed in accordance with multiple nodes of the graph model. Node groupings can be effected (for example) by associating logic operators with edges connecting the nodes and/or with the nodes themselves. For example, FIG. 2 depicts a node that indicates that an "OR" logic operator is to be effected by determining whether the entity is at least one of: having avoided taking Tysabri® and being JC virus negative.

If the entity's data record does not include medication data and/or data indicating whether the entity has the JC virus, node data may indicate that this criteria cannot be evaluated. The criteria-group score for the corresponding group (associated with the "OR" node) may be assigned a lower value than if data had been available and had indicated that the criteria was satisfied. In some instances, the criteria-group score for the corresponding node (associated with the "OR" node) may be assigned a higher value than if data had been available and had indicated that the criteria was not satisfied.

Thus, a criteria-group score can be generated for each criteria group associated with the particular investigatory event. A score for the entity-event pair can then be generated based on the aggregated criteria-group scores. For example an entity-event score may be generated by summing or averaging criteria-group scores. In some instances, various criteria-groups are assigned corresponding weights (e.g., as indicated by user input to reflect an importance of satisfying a criteria group, based on population data, etc.), and an entity-event score may be generated by performing a weighted sum.

By representing data for multiple investigatory events in this graph format, a single graph model can be used repeatedly for many entities and at multiple points in time. The graph model can then facilitate reducing or eliminating processing that requires evaluation of investigatory-event criteria for a large list of diseases to be repeatedly integrated with entity-specific data structures and/or that requires repeatedly retrieving disease and entity data. Not only can this efficient representation reduce the space required for the graph model, but further, a given individual node and/or edge may be part of multiple branches associated with multiple investigatory events. Thus, a single evaluation of a criteria for the individual node and/or edge can be used during evaluation of multiple investigatory events. Further, various potential trajectories can be evaluated using different machines, such that parallel processing is enabled.

Figure 3:
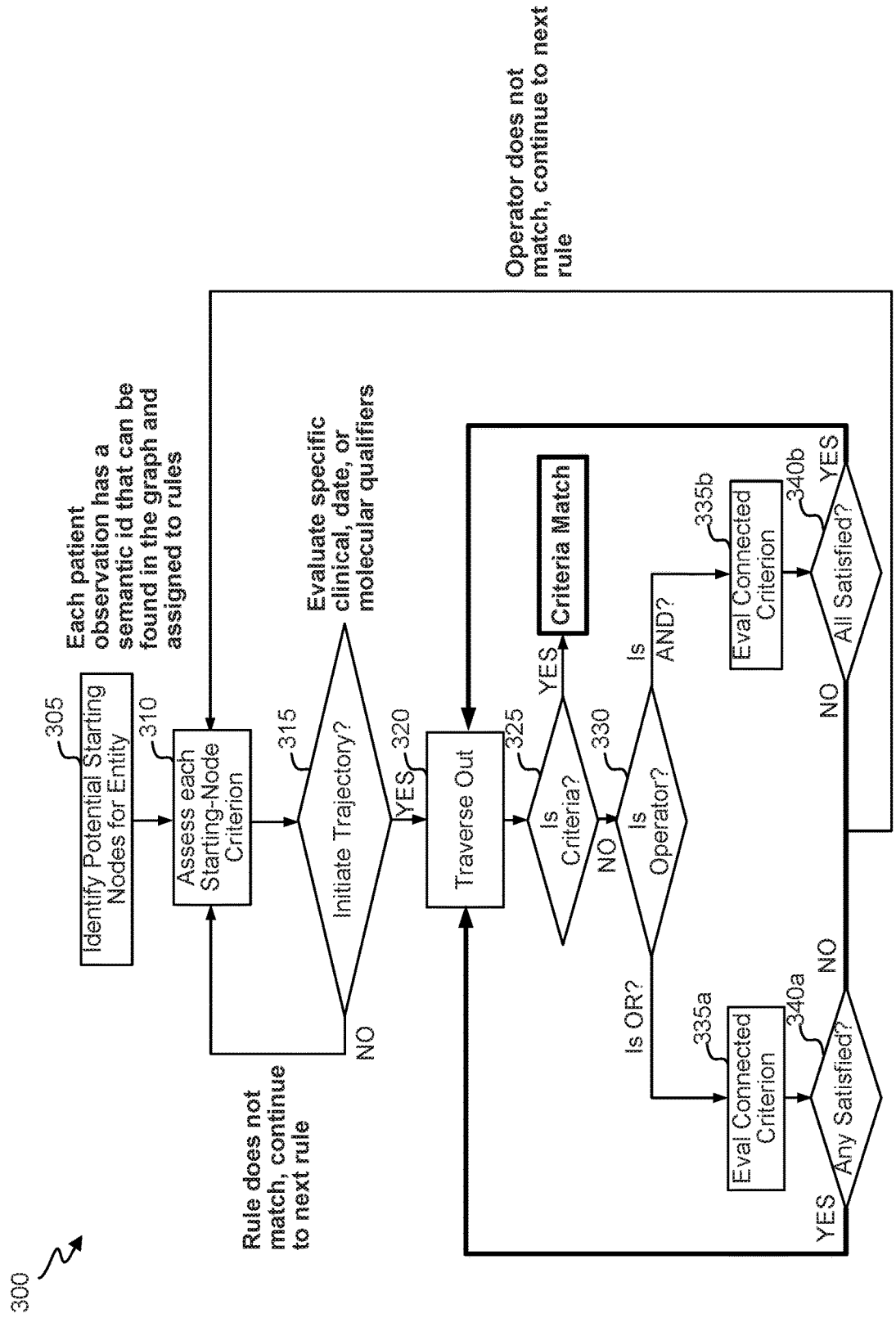
FIG. 3 shows a process for using a graph model to identify investigatory-event matches for an entity.

FIG. 3 shows a process 300 for using a graph model to identify investigatory-event matches for an entity. At block 305, one or more starting nodes within a graph model are identified that pertain to key-value pairs associated with a particular entity. For example, electronic data for an entity may include one or more semantic identifiers (e.g., included in one or more key-value pairs), each of which can represent a physical characteristic or category thereof. A semantic identifier can represent (for example) a disease, medical condition, ailment, age, weight, and so on. An incomplete subset of a set of nodes in a graph model can be designated (e.g., via metadata) as starting nodes, each of which can be associated with a semantic identifier (e.g., included in a criterion or criteria group of the node).

The one or more starting nodes can be identified as each starting node for which one, more or all of the semantic identifiers identified in a criteria group of the starting node are also present in the entity data. In some instances, the one or more starting nodes are identified as each starting node for which one, more or all of the criteria includes a constraint on a value type (e.g., as indicated by a corresponding semantic code) that is also present in the entity data. For example, the one or more starting nodes may include a starting node having a constraint: "symptom=blindness" if entity data includes any key-value pair that includes a key corresponding to (or set to) "symptom". In some instances, the one or more starting nodes are identified as each starting node for which one, more or all of the criteria includes a constraint that specifies a value type or a value (e.g., via a corresponding semantic code) that is also present in the entity data. Thus, in the above example, the one or more starting nodes may include the exemplary starting node so long as the entity data included any semantic code (e.g., as part of a key or as part of a value) that corresponded to (or that was set to) "symptom" or "blindness". In some instances, the one or more starting nodes are identified as each starting node for which one, more or all of the criteria includes a specific constraint that is also present in the entity data. Thus, in the above example, the one or more starting nodes may include the exemplary starting node so long as the entity data included a semantic code (e.g., as part of a value) that corresponded to "blindness".

Notably, the identification of the one or more starting nodes need not be performed by assessing criteria associated with all nodes in a graph model. Rather, nodes designated as starting nodes can be selectively assessed. A node may be designated as a starting node in response to (for example) detecting an input corresponding to an indication that a criterion or criteria group of the node is a fundamental focus of one or more investigational events (e.g., in association with inputs initially defining the one or more investigational events); determining (e.g., based on population data or past trajectory data) that a criterion or criteria group of the node is the most limited amongst criteria associated with one or more investigational events); and/or determining that an edge of at least one investigatory-event branch is positioned at the node. The one or more starting nodes may (for example) include an incomplete subset of the starting nodes in the graph model, such as only those starting nodes for which there is overlap (e.g., and possibly complete overlap) between the semantic identifier(s) included in the criteria group of the starting nodes and the electronic data of the entity.

Thus, for example, a first starting node may be identified that includes a criterion requiring a diagnosis a particular disease (as indicated by a first semantic identifier) that is also included in the entity data, and another starting node may be identified that corresponds to an age constraint (e.g., such that each of the other starting node and the entity data include a semantic identifier indicating that a corresponding value or specification relates to an age data type).

At block 310, for each of the one or more starting nodes, each criterion associated with the starting is assessed using the entity data to determine whether to initiate a trajectory from the starting node in association with the entity. In some instances, a mere match of the semantic identifiers is sufficient to identify a starting node (e.g., which a semantic identifier match included matching a semantic identifier specified in a constraint of a single criterion with a semantic identifier in the entity data). In some instances, an entity-data value associated with the semantic identifier is to be further assessed in accordance with one or more criteria of the starting node. For example, a criterion may indicate that an entity is not to merely have any age but is to be 18 years old or older.

At block 315, for each of the one or more starting nodes, it is determined whether to initiate a trajectory from the starting node in association with the entity. It can be determined to initiate the trajectory if it is determined, at block 310, that the criteria group of the starting node is satisfied. Conversely, it may be determined that the trajectory is not be initiated if it is determined, at block 310, that the criteria group of the starting group is not satisfied.

If the trajectory is initiated, process 300 proceeds to block 320 to traverse out from the starting node. The outward traversal can extend along an edge included in an investigatory-event branch and that is connected to the starting node. In some instances, one, more or all edges in a graph model are directional, such that a trajectory only extends along an edge having that connects to a present node with a receiving end and that points to another node. In some instances, a single starting node may serve as a starting node for multiple investigatory-event branches. In these instances, when the branches diverge (e.g., at the starting node or at another node), a trajectory may split or a duplicate trajectory may be generated that can be assigned to one of the diverging edges while an initial trajectory can be assigned to another of the diverging edges.

At block 325, it is determined whether the edge and other node represent a criterion or criteria group. If so, the criterion or criteria group can be evaluated via the assessment depicted in a process 400 depicted in FIG. 4. If not, process 300 continues to determine whether the edge and other node represent one or multiple specific operators at block 330. Each of the specific operators may include a logical operator or Boolean operator.

In the depicted instance, if the edge and other node represent an "OR" operator, process 300 continues to block 335*a*, at which the criteria (or criteria groups) connected to the operator and evaluated. For example, the other node may be connected to multiple nodes, each of which represent a criteria group (including one or more criteria). At least one (or all) of the criteria group can be evaluated (e.g., in a manner similar to the processing depicted in FIG. 4) to determine whether any criterion of the criteria group are satisfied.

At block 340*a*, it is determined whether any of the connected criteria (or criteria groups) connected to the operator are satisfied. If so, process 300 can return to block 320, such that the trajectory can be further extended. Otherwise, the trajectory can terminate, and process 300 can return to block 310 to assess another of the one or more starting nodes (or process 300 can end if there are no remaining starting nodes of the one or more starting nodes).

In the depicted instance, if the edge and other node represent an "AND" operator, process 300 continues to block 335*b*, at which the criteria (or criteria groups) connected to the operator and evaluated. For example, the other node may be connected to multiple nodes, each of which represent a criteria group (including one or more criteria). All criteria of the criteria group can be evaluated (e.g., in a manner similar to the processing depicted in FIG. 4), potentially individually, to determine whether the criteria are satisfied. At block 340*b*, it is determined whether all of the connected criteria (or criteria groups) connected to the operator are satisfied. If so, process 300 can return to block 320, such that the trajectory can be further extended. Otherwise, the trajectory can terminate, and process 300 can return to block 310 to assess another of the one or more starting nodes (or process 300 can end if there are no remaining starting nodes of the one or more starting nodes).

To reduce duplicate processing, data from individual traversals of the graph model can be saved in association with an entity identifier. For example, a binary result can be stored in association with each node of one or more nodes to indicate whether a criteria group of the node was satisfied with respect to a given entity. As another example, a past graph trajectory can be saved. The trajectory can indicate that multiple criteria groups associated with multiple nodes along the trajectory were satisfied and potentially an indication as to whether a criteria group associated with an end node of the trajectory was satisfied. This data can allow a next iteration to skip analysis of at least some criteria group, which may relate to one or more other investigatory events. In some instances, each node can be associated with an indication as to what types of entity data are evaluated. When a new communication or entity record indicates that a particular type of entity data has been updated since a previous evaluation of a given criteria group that relies upon the particular type of entity data, a new assessment may be performed for a previously evaluated node associated with the criteria group. In some instances, a saved result indication (e.g., indicating a result of evaluation of a criteria group) or saved trajectory can have an expiration time period or date, such that node evaluations performed subsequent to the time period or date are to be performed again and/or such that a new retrieval of entity data is to be performed to evaluate the associated criteria group(s).

As a result of time-synchronized processing or discrete processing, evaluations corresponding to a single node in a graph model can be performed for many entities using the entities' corresponding entity codes. For each of these entities, a respective evaluation can indicate whether a criterion specified in association with the node was satisfied. Further, for each of these entities, one or more other characteristics of the entity may be determinable (e.g., based on electronic entity data). Thus, the cross-entity evaluations can be used to generate one or more statistics or distribution that correspond to the node-associated criterion. As one example, a statistic can be generated that indicates a percentage of all of the many entities (or a specified sub-group of the many entities) for which a criteria group was satisfied. As another example, a distribution can be generated for a variable (e.g., value in a key-value pair) that is assessed in the criteria group. The statistic and/or distribution may be useful to inform an investigatory-event investigator as to an impact that a corresponding criterion may have on a size of a population that is eligible for an investigatory event.

In some embodiments, a graph model is used to generate population analytics that may be used to characterize an ongoing study or inform the definition of criteria for a new investigatory event. For example, previous traversal data through a part of the graph model can indicate a portion or number of entities for which a particular criterion or type of criteria or criteria group was satisfied, which may be used to predict an impact that a same or similar particular criterion, type of criteria or criteria group would have in terms of identifying eligible entities for an investigatory event. The prediction may include (for example) a number of entities for which the criterion will be satisfied during a predefined time period (or time period identified via input from an investigator user) or a time period required to identify at least a predefined threshold number of entities for which the criterion is satisfied.

Figure 4:
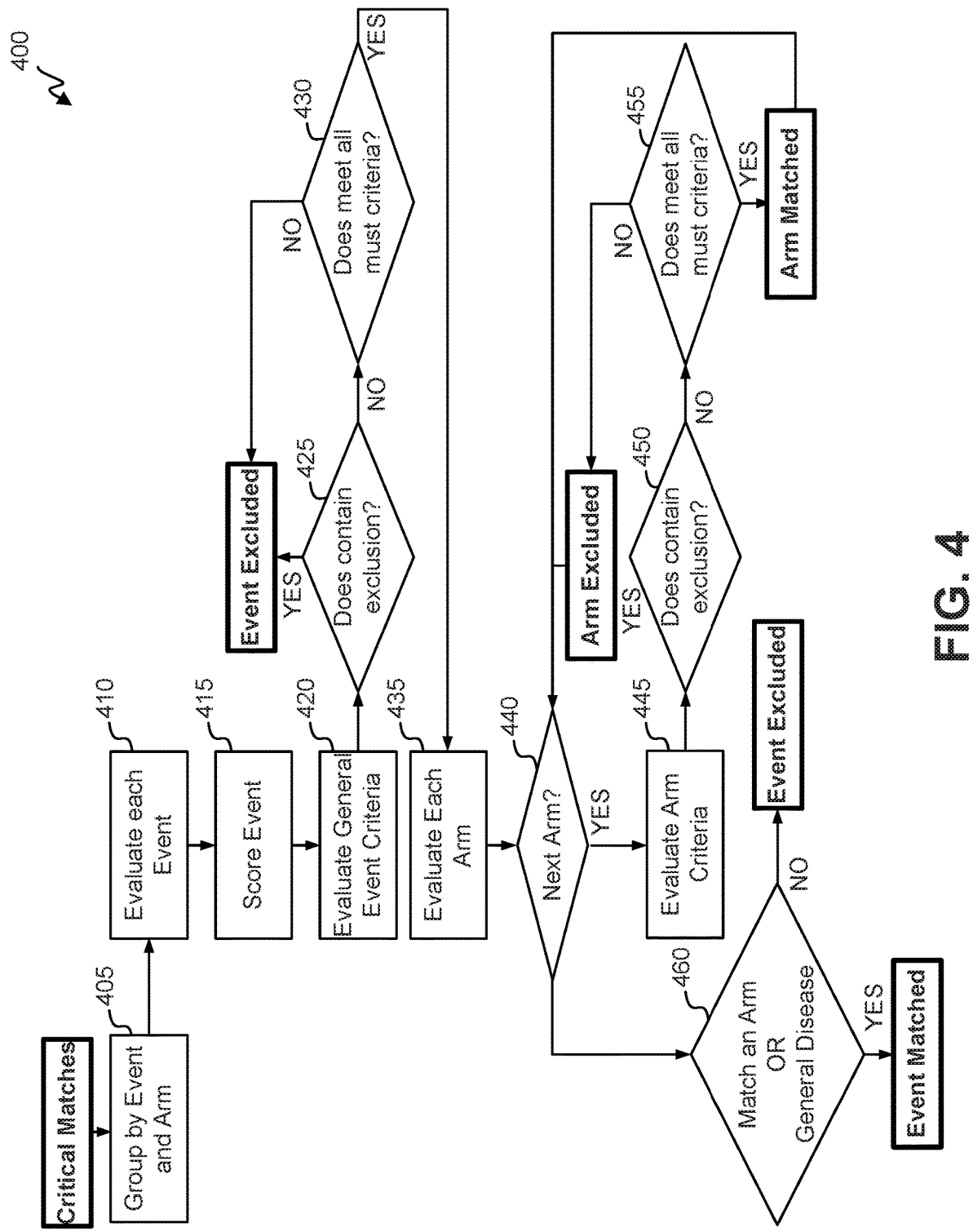
FIG. 4 shows process for evaluating criteria in accordance with some embodiments.

FIG. 4 shows process 400 for evaluating criteria in accordance with some embodiments. At block 405, criteria from one or more rules (corresponding to one or more investigatory events and one or more arms) to be evaluated for an entity is collected and (if applicable) separated by investigatory event and/or arm. At block 410, a processing is initiated to assess criteria for each particular investigatory event's rule(s). At block 415, a score is generated for a given investigatory event. The score can depend on which data elements corresponding to a investigatory event are present in entity data. For example, an investigatory event may be associated with a criterion relating to a CT scan. If data for the specified type of CT scan is absent from an entity record, it may negatively influence a score. An extent to which it negatively influences a score may depend on a weight associated with the criteria.

At block 420, general investigatory-event criteria is evaluated. The general investigatory-event criteria can include (for example) one or more inclusion criteria and/or one or more exclusion criteria. Each criteria may have been defined based on user input. User input may further indicate, for each of one or more of the criteria, that the criterion is to be an absolute exclusion criterion (or an absolute inclusion criterion). User input may indicate that each of one or more criteria is to be neither an absolute exclusion criterion or absolute inclusion criterion (or a lack of an indication that that a criterion is to have either absolute designation may provide this information). Evaluating a criterion can include identifying entity data that corresponds to the criterion and determining—based on the entity data—whether the criterion is satisfied. At block 425, it is determined whether a result of the evaluation includes an exclusion (that is, whether an exclusion criterion was satisfied). If so, the investigatory even can be eliminated as a possible match for the entity. Otherwise, process 400 proceeds to block 430 where it is determined whether all "must" criteria were met via the evaluation. If not, the investigatory event can be eliminated as a possible match for the entity. Otherwise, process 400 proceeds to block 435.

In some instances, an investigatory event may have distinct criteria for different arms in a study. In these instances, arm-specific processing is initiated at block 435. At block 440, a first arm is identified, and criteria for the arm are evaluated using entity data at block 445. At block 425, it is determined whether a result of the evaluation includes an exclusion (that is, whether an exclusion criterion was satisfied). If so, the arm is excluded and process 400 proceeds to block 440, where it is determined whether the investigatory event includes another arm for which to evaluate criteria. Otherwise, process 400 proceeds to block 455 where it is determined whether all "must" criteria were met via the evaluation. If not, the arm is excluded. Otherwise, the arm is identified as a match. In either instance, process 400 returns to block 440, where it is determined whether the investigatory event includes another arm for which to evaluate criteria. When each arm has been assessed, process proceeds to block 460, where it is determined whether an arm and/or the general investigatory event was identified as a match or possible match for an entity.

Figure 5:
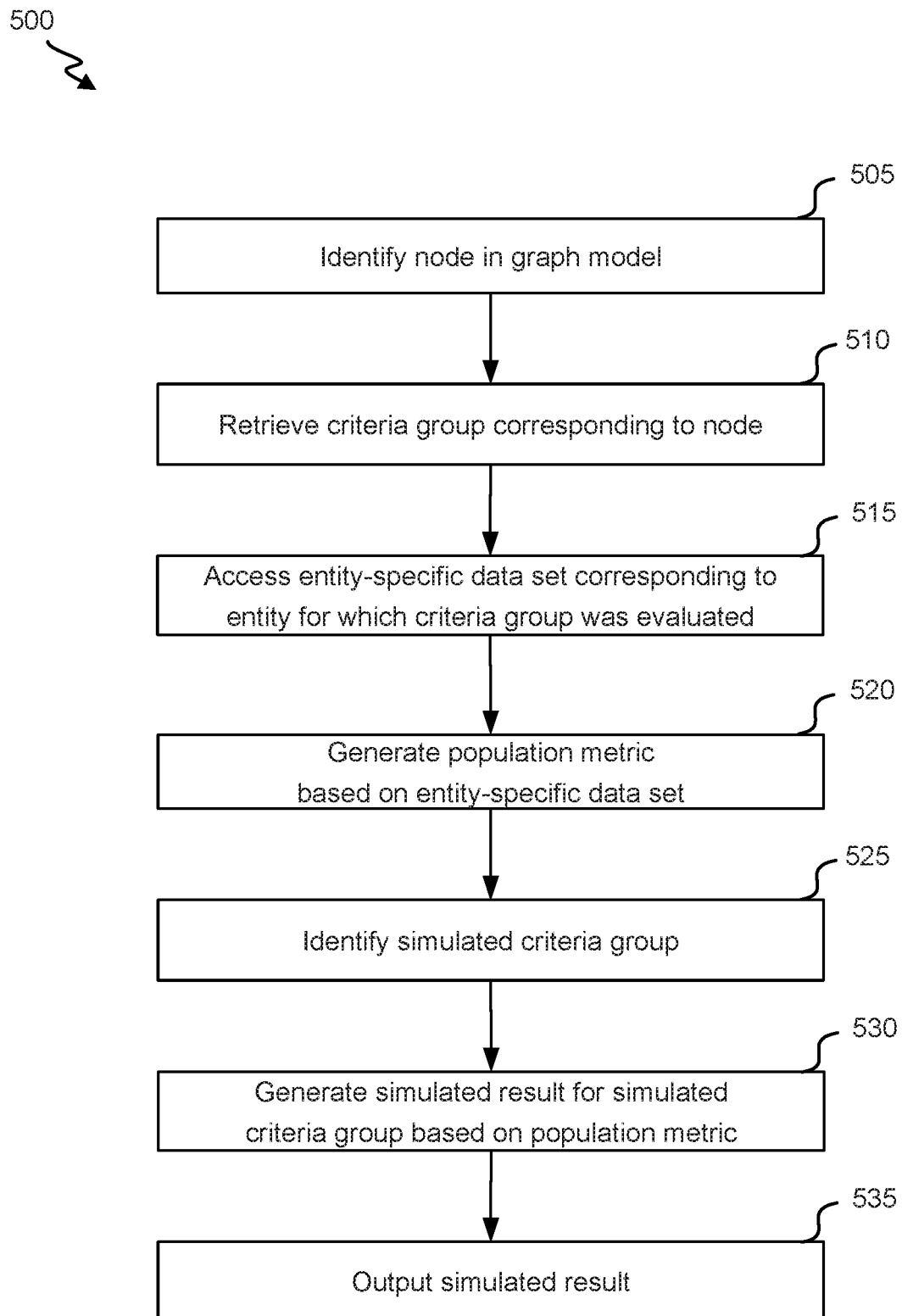
FIG. 5 shows a flowchart of a process for generating a simulated result based on graph-model iterations in accordance with some embodiments.

FIG. 5 shows a flowchart of a process 500 for generating a simulated result based on graph-model iterations in accordance with some embodiments. Process 500 begins at block 505 where a node in a graph model is identified. The graph model can include a set of nodes and a set of edges. Each edge of the set of edges can connect two nodes of the set of nodes. The graph model can be configured such that a trajectory extends to a next node when a criteria group (e.g., including a single criterion or multiple criteria) specified by the next node and/or a criteria group (e.g., including a single criterion or multiple criteria) specified by a connecting edge is satisfied. The graph model can include a plurality of end nodes. Each end node of the plurality of end nodes can identify an investigatory event (e.g., via a coded identifier of the event). The graph model can include a model that relates to multiple diseases, medical conditions and/or symptoms.

The node can include one associated with a criteria group relating to one or more particular types of entity characteristic(s). The particular characteristic can include one (for example) identified (via input) by a user and/or included in a preliminary or actual criteria group for a new investigatory event. [0030] In some instances, criteria groups associated with each of a plurality of nodes in the graph model are identified, and the criteria groups are then filtered with respect to a given entity based on whether entity data for the entity includes each type of the particular type(s) of entity characteristic(s) identified in the criteria group. Thus, the node identified at block 505 can include one corresponding to one or more entity-characteristic types that are also included in the entity data.

In some instances, the particular characteristic(s) can be defined as (for example) corresponding to a particular type of characteristic and a particular constraint for the characteristic type. The particular characteristic(s) can be defined (for example) based on input provided at a webpage, such as a selection of a characteristic type from amongst multiple types of characteristics includes in a list or pull-down menu, typing an code for a characteristic type in a text field, typing a specific value or value threshold in a text field, or identify a threshold for a value of the characteristic using a slider input tool As other examples, the characteristic type and/or constraint can be determined by extracting the information from a file or received communication. In some instances, identification of a given constraint is made in accordance with a standardized format (e.g., to require an identifier of a characteristic type to be one of a predefined list of characteristic-type identifiers). The input, file and/or communication may have been associated with a user coordinating and/or involved with selecting entities for a given investigatory event or a user with authorization to define or modify the graph model.

It will be appreciated that a single node can correspond to criteria applicable to multiple investigatory events. Associating a given investigatory event with a node may be performed in an automatic or semi-automatic manner. For example, one or more inputs or files may be received that identify a set of criteria groups (e.g., each including one or more criteria) to be assessed (e.g., sequentially assessed in an identified order, sequentially assessed in an order to be automatically determined or concurrently assessed). An event mapping system may then determine, for each of the set of criteria groups (or each criterion within the set of criteria groups), whether an existing node in a graph model corresponds to a same (or similar within a defined degree) criteria group (or criterion). If so, an identifier of the investigatory trial can be linked to an identifier of the node. If not, a new node can be generated that corresponds to the criteria group (or criterion).

The node identification performed at block 505 can include identifying a starting node for which the criteria group is satisfied based on particular entity data. A node in the graph model may be designated as a starting node if it is a first node in a path terminating at an end node (e.g., and thus for which an edge corresponding to a given investigatory event extends from the node but no edge corresponding to the given investigatory event extends from another node to the node). Edges between the event-associated nodes can be formed (for example) when each criteria group is mapped to a new or existing node (or as the mapping is occurring). In some instances, an edge can be multi-purposed to apply to the investigatory event in addition to one or more other investigatory events. Nodes can be connected with edges in accordance with a particular protocol. For example, edges may be generated such that criteria groups are evaluated in an order corresponding to a predicted degree to which a criteria group will filter an entity group (e.g., such that edges are formed to cause more restrictive criteria groups being evaluated before less restrictive criteria groups). As another example, edges may be generated such that criteria groups are evaluated in an order corresponding to indicated importances of various criteria groups that pertain to an investigatory event (e.g., as conveyed via input and/or such that edges are formed to cause more important criteria groups to be evaluated before less important criteria groups). As yet another example, edges may be generated such that criteria groups are evaluated in an order corresponding to predicted availability of entity data to be assessed by the criteria groups (e.g., such that edges are formed to cause criteria groups associated with higher predictions of data availability to be evaluated before criteria groups associated with lower predictions of data availability).

At block 510, a criteria group that corresponds to the node is retrieved (e.g., by querying a data store using an identifier of the node). The criteria group can include (for example) one or more criteria—each of which can identify a type of entity characteristic and constraint on the same. The criteria group can include a constraint associated with the particular type of characteristic. For example, the node may have been identified due to the criterion relating to age, and block 510 can determine that the criteria group for the node specifies that an entity's age must be between 18 and 30. Notably, in instances in which block 505 includes identifying a node as one that relates to a particular characteristic in a (preliminary or actual) criteria group associated with a new investigatory event, a constraint on the particular characteristic as set forth in the criteria group for the new investigatory event need not be the same as a constraint on the particular characteristic as set forth in a criteria group associated with the node.

At block 515, entity-specific data is accessed. More specifically, iteration data that includes a set of entity-specific data points can be accessed. Each entity-specific data point in the entity-specific data can correspond to an entity for which the criteria group has been evaluated, and each entity-specific data point can correspond to the criteria group. For example, an entity-specific data point can include a binary indication as to whether the criteria group (or a criterion within the criteria group) was satisfied for the corresponding entity. As another example, the entity-specific data point can include an entity characteristic used in an evaluation of whether the criterion was satisfied. The entity-specific data may correspond to iteration data associated with a single investigatory event or iteration data associated with multiple investigatory events (e.g., each of which are associated with the criteria group).

The entity-specific data point may further include related information, such as a time at which the criterion was evaluated. Notably, the set of entity-specific data points need not only include data points corresponding to entities for which the criterion was satisfied.

At block 520, a population metric is generated based on the iteration data. The population metric can include a distribution or statistic based on the set of entity-specific data points. In some instances, the population metric can include a percentage of entities for which the criteria group was satisfied and/or a rate at which criteria-group satisfaction was detected for individual entities. In some instances, the population metric includes a distribution, characteristic of a distribution, or a statistic of the characteristic (across all of the data points, across the data points associated with satisfaction of the criteria group, and/or across the data points associated with the criteria group not being satisfied). The statistic can include (for example) a mean, median, mode, variance, standard deviation or range.

At block 525, a simulated criteria group is identified. The simulated criteria group can be the same or different than the retrieved criteria group. The simulated criteria group can include one used to identify the node in block 505. The simulated criteria group can include a preliminary or actual criteria group of new investigatory event. The simulated criteria group can be based on a constraint on a same type of characteristic as associated with the criteria group for the identified node (e.g., and one identified as a preliminary or actual criteria group of a new investigatory event). The constraint may include a same or different constraint (e.g., one or more same or different thresholds) than the constraint in the criteria group for the identified node.

At block 530, a simulated result is generated for the simulated criteria group based on the population metric. Generating the simulated result can include performing an extrapolation or interpolation technique. Generating the simulated result can include generating a distribution and/or model based on values of the characteristic in the entity-specific data set, and identifying a number or percentage associated with a constraint of the simulated criterion based on the distribution and/or model. The simulated result may, but need not, correspond to a same type of variable as the population metric. The simulated result may include (for example) a predicted percentage of an entity population for which the simulated criteria group will be satisfied, a predicted time period of identifying a predefined number of entities for which the simulated criteria group will be satisfied, and/or a predicted number of entities within an entity population for which the simulated criteria group will be determined to be satisfied within a predefined time period.

In some instances, the simulated result also depends on one or more other simulated criteria groups. For example, a simulated investigatory even may include a set of simulated criteria groups (with each simulated criteria group of the set of simulated criteria groups including one or more criteria)—one of which is the simulated criteria group. The simulated result may then identify (for example) a predicted percentage of an entity population who will be eligible for and/or accepted to the simulated investigatory event, a predicted time period of identifying a predefined number of entities who will be eligible for and/or accepted to the simulated investigatory event, and/or a predicted number of entities within an entity population who will be eligible for and/or accepted to the simulated investigatory event within a predefined time period.

At block 535, the simulated result is output. For example, the simulated result can be presented at a local or remote interface and/or transmitted to another device. The simulated result may be presented concurrently with an option to modify the simulated criteria group. Detecting a modification can trigger part or all of process 500 to be repeated. In some instances, an interface presents a high-level simulated result that corresponds to a predicted number or percentage of entities that correspond to all criteria groups identified for a preliminary or actual investigatory event and further identifies—for each individual criteria group identified for the event—a degree to which the individual criteria group is limiting the predict number of percentage relative to the other criteria groups. This further identification can be conveyed (for example) by presenting, in association with a representation of each criteria group, a number, color, size, or text descriptor that indicates a degree to which it is contributing to overall limiting of a size of a simulated result.

In some instances, a graph model can be used to iteratively evaluate whether a specified mutation is detected. The iterative analysis can include first determining whether a particular type of mutation has been observed and then identifying whether the mutation occurs within a particular region (e.g., of the genome, epigenome, etc.) or an assessment performed in the reverse order. In some instances, a graph model can be used to represent class-level constructs, such as molecular alteration groups. For example, directionality of edges can facilitate representing an ordered series of molecular alterations (e.g., with respect to a set of nodes).

Figure 6:
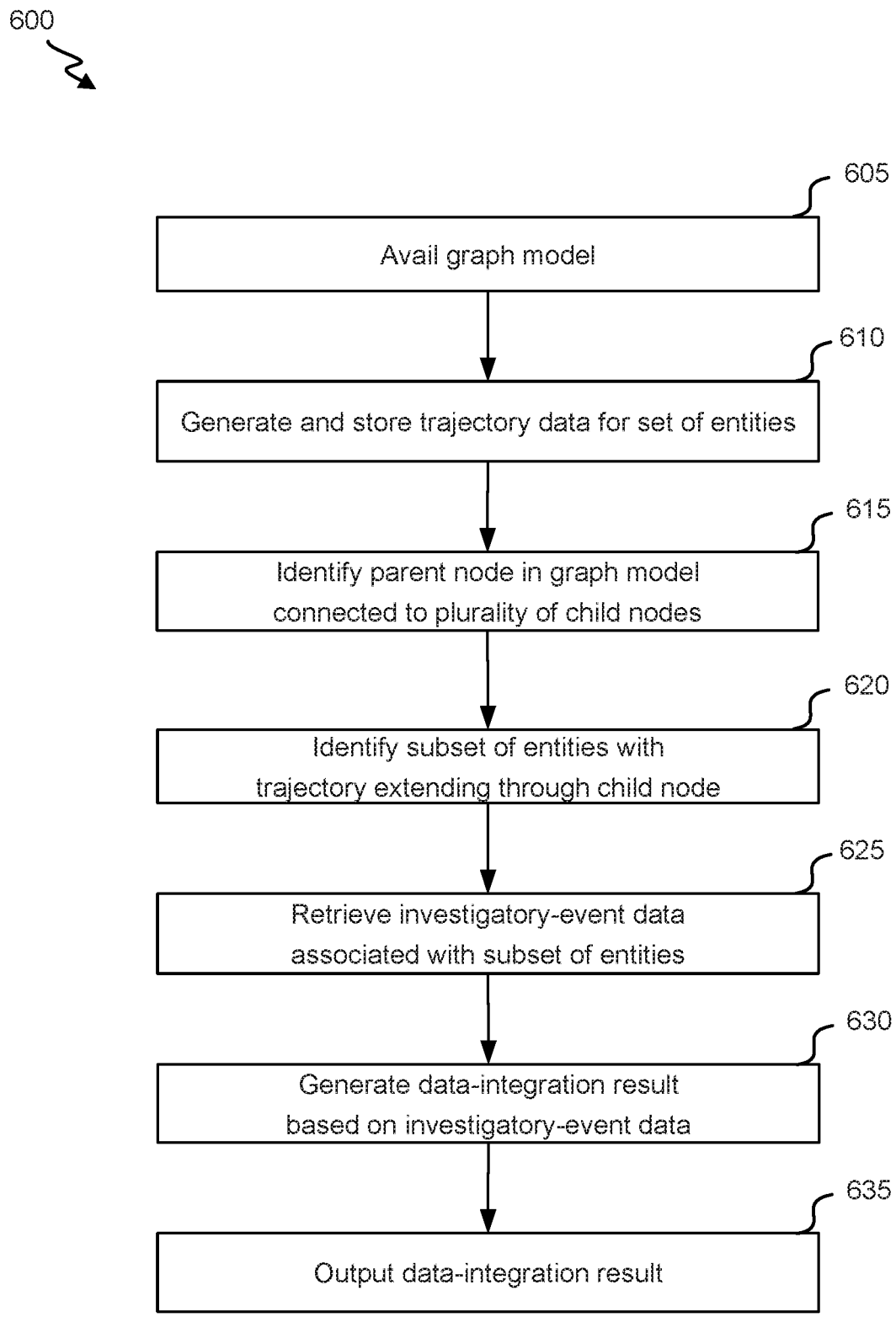
FIG. 6 shows a flowchart of a process for using a structured graph model to perform a meta-analysis on related investigatory-event data in accordance with some embodiments.

FIG. 6 shows a flowchart of a process 600 for using a structured graph model to perform a meta-analysis on related investigatory-event data in accordance with some embodiments. End nodes of a graph model can represent (or be connected to investigatory-event-specification nodes that represent) investigatory-event details. These nodes can also be connected to indicate a relationship between specification of different investigatory events.

Process 600 begins at block 605 where a graph model is availed. The graph model can include a set of nodes and a set of edges. Each edge of the set of edges can connect two nodes of the set of nodes. The graph model can be configured such that a trajectory extends to a next node when a criterion specified by the next node is satisfied. The graph model can include a plurality of end nodes. Each end node of the plurality of end nodes can identify identifying a investigatory event.

At block 610, trajectory data for each of a set of entities is generated and stored. Block 610 can include performing, for each entity of the set of entities, a set of actions. The set of actions can include identifying one or more starting nodes from amongst the set of nodes based on first electronic data associated with the entity. The set of actions can further include generating one or more trajectories based on second electronic data associated with the entity. Each trajectory of the one or more trajectories can extend from a starting node of the one or more starting nodes through one or more edges and one or more other nodes. An extension of any trajectory through a traversed edge or node can identify that at least part of the second electronic data satisfies any criteria group and/or rule specified by the traversed edge or node. For example, the starting node identified for the entity can be connected (via a corresponding edge) to each of a set of other nodes. Trajectory data is then generated that characterizes each of the one or more trajectories (e.g., identifying a final node where the criterion was satisfied or identifying a first node where the criterion was not satisfied). The trajectory data may include a criteria-group score or a score associated with an entity-event pair. The trajectory data may be indicative of a investigatory event (or each investigatory event) for which the entity was eligible or enrolled. The trajectory is then stored in association with an identifier of the entity.

At block 615, a parent node is identified in the graph model from amongst the set of nodes in the graph model. Identifying the parent node can include (for example) evaluating a connection structure and/or hierarchical structure of the graph model, navigating at least part of the graph model, evaluating and/or compare node-associated criteria group and/or generating a new parent node associated with a criteria group that corresponds to an overlap between criteria groups of other nodes. The parent node can correspond to an investigatory-event specification of interest for a meta-analysis. The parent node can be connected to a plurality of child nodes via a corresponding edge. Each of the plurality of child nodes can be associated with a corresponding investigatory-event specification that is more specific than an investigatory-event specification associated with the parent node. For example, each child node of the plurality of child nodes can correspond to a drug type that it is a sub-type of a drug type associated with a parent node. As another example, each child node of the plurality of child nodes can correspond to a procedure type that is more specific (e.g., in terms of a type or position) than a procedure type associated with the parent node. As yet another example, each child node of the plurality of child nodes can correspond to a disease type that is more specific (e.g., in terms of a type or position) than a disease type associated with the parent node. In some instances, each of the plurality of child nodes is an end node associated with an investigatory event.

At block 620, a subset of the set of entities is identified based on the stored trajectory data. Trajectory data for each entity in the subset can indicate that a trajectory associated with the entity extended through a child node of the plurality of child nodes and/or that the trajectory successfully reached the child node. For example, the trajectory data can indicate that a trajectory reached an end node that is the child node. Thus, the subset can include all entities where a trajectory reached an end node corresponding to an identification of an investigatory event with a specification that corresponds to a specification of a meta-analysis. In some instances, the subset is defined to include all entities actually enrolled in an investigatory event represented by a child node of the plurality of child nodes) or—in some instances—an investigatory event represented by the parent node.

At block 625, investigatory event data associated with the subset of the set of entities is retrieved. In some instances, the investigatory event data includes data indicating an arm to which the entity was assigned in the investigatory event and/or one or more results of the investigatory event (e.g., indicative of a disease progression, side effect, etc.). Other entity data can further be retrieved, such as each entity's age, other medical conditions, medication history, health metrics, etc.

At block 630, a data-integration result is generated based on the investigatory event data. The data-integration result can be generated to correspond with an investigatory-event specification associated with the parent node. For example, by analyzing data corresponding to various investigatory events using different drugs of a particular type, a data-integration result may indicate an efficacy of the particular type. The result may be generated by, for example, generating one or more weighted averages, identifying one or more weights, identifying one or more statistical-significance values, etc.

At block 635, the data-integration result is output. For example, the data-integration result may be transmitted to another device or locally presented.

A size of a population that is eligible for an investigatory event is highly dependent on a stringency of eligibility requirements. A small population may result in (for example) poor statistics and/or a long investigatory-event duration. A large population may result in a confounded analysis. One approach for tailoring the population size is to perform simulations to prospectively predict population sizes in view of potential constraints.

Another approach for tailoring the population size is to generate a score for each entity of a set of entities. A relative or absolute investigatory-event threshold can be set, such that entities with scores above the threshold are determined to be eligible for the investigatory event. For example, a relative investigatory-event threshold can be generated to indicate that predefined number of people with the highest scores in a predefined time period are to be eligible for the investigatory event. In this process, it may be desirable to differentially weight different eligibility factors such that important factors are preferentially weighted. Further, the differential weighting can facilitate handling instances where entity data corresponding to specific criteria are missing (e.g., to reduce a penalty of missing data when population data indicates that most entities have conforming characteristics with respect to a criteria group).

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method comprising:
   availing a graph model, wherein the graph model includes a graph structure that connects a set of nodes and a set of edges, each edge of the set of edges connecting two nodes, the set of nodes including a plurality of end nodes, each end node of the plurality of end nodes identifying a clinical investigatory event;
   for each entity of a set of entities:
      identifying a starting node from amongst the set of nodes based on first electronic data associated with the entity;
      generating one or more graph-structure trajectories through part of the graph structure based on second electronic data associated with the entity, each graph-structure trajectory of the one or more graph-structure trajectories extending from the starting node through one or more edges and connecting to one or more other nodes of the set of nodes, wherein generating the one or more graph-structure trajectories includes iteratively determining, for each graph-structure trajectory of the one or more trajectories, whether to extend the graph-structure trajectory to a next node in a path based on at least part of the second electronic data and a criteria group of the next node until the graph-structure trajectory terminates; and
      storing graph-structure trajectory data characterizing each of the one or more graph-structure trajectories in association with an identifier of the entity;
   identifying a parent node connected to a plurality of child nodes via a corresponding edge, each of the plurality of child nodes being associated with a corresponding clinical-trial-participation criterion that is more specific than a clinical-trial-participation criterion associated with the parent node;
   identifying a subset of the set of entities based on the stored graph-structure trajectory data, wherein graph-model trajectory data for each entity in the subset indicates that a graph-structure trajectory associated with the entity connected to a child node of the plurality of child nodes and that the clinical-trial-participation criterion associated with the parent node is satisfied with respect to the entity;
   retrieving investigatory-event data associated with the subset of the set of entities, wherein the investigatory-event data includes information indicative of one or more results corresponding to multiple clinical investigatory events corresponding to multiple end nodes, wherein, for each entity in the subset of the set of entities, a graph-structure trajectory of the one or more graph-structure trajectories associated with the entity connects the child node to an end node of the multiple end nodes, the plurality of end nodes including the multiple end nodes;
   generating, based on the investigatory-event data, a data-integration result, wherein the data-integration result is generated to correspond with the clinical-trial-participation criterion associated with the parent node; and
   outputting the data-integration result.

2. The computer-implemented method as recited in claim 1, wherein the iterative determination of whether to extend the graph-structure trajectory includes determining to terminate the graph-structure trajectory when the trajectory has reached an end node of the plurality of end nodes or when a result of an assessment of the criteria group using the at least part of the second electronic data indicates that:

if the criteria group is an inclusion criteria group, the criteria group is not satisfied; or if the criteria group is an exclusion criteria group, the criteria group is satisfied.

3. The computer-implemented method as recited in claim 1, wherein:

the clinical-trial-participation criterion associated with the parent node indicates a first type of condition;

the corresponding clinical-trial-participation criterion associated with each of the plurality of child nodes indicates a corresponding second type of condition; and each of the corresponding second type of condition is a sub-type of the first type of condition;

each of the plurality of child nodes includes an end node identifying a corresponding clinical investigatory event that involves investigating a particular type of treatment, the particular type of treatment being the same across the plurality of child nodes; and the data-integration result includes a result of treating the first type of condition with the particular type of treatment.

4. The computer-implemented method as recited in claim 1, wherein:

each of the plurality of child nodes includes an end node;

the corresponding clinical-trial-participation criterion associated with each of the plurality of child nodes indicates a type of treatment provided during the clinical investigatory event identified by the child node, the indicated types of treatment being different across the plurality of child nodes but corresponding to a particular treatment class that is the same across the plurality of child nodes;

the clinical-trial-participation criterion associated with the parent node indicates the particular treatment class;

for each child node of the plurality of child nodes, the clinical investigatory event identified by the child node corresponds to a particular type of disease that is the same across the plurality of child nodes; and the data-integration result includes a result of treating the particular type of disease with the particular treatment class.

5. The computer-implemented method as recited in claim 1, wherein the data-integration result includes one or more weights or one or more coefficients, wherein each of the one or more weights or one or more coefficients indicates a degree to which a corresponding entity attribute statistically relates to an investigatory-event outcome.

6. The computer-implemented method as recited in claim 1, wherein identifying the parent node includes:

determining that the corresponding clinical-trial-participation criterions associated with the plurality of child nodes are related; and generating the parent node and generating a set of new edges to connect the parent node to the plurality of child nodes.

7. The computer-implemented method as recited in claim 1, wherein:

each of the plurality of child nodes includes an end node;

for a first child node of the plurality of child nodes, the corresponding clinical-trial-participation criterion associated with the first child node includes a first value that conforms with a first controlled vocabulary; and for a second child node of the plurality of child nodes, the corresponding clinical-trial-participation criterion associated with the second child node includes a second value that conforms with a second controlled vocabulary, the first controlled vocabulary being different than the second controlled vocabulary, and the first value and second value representing a similar or same condition or treatment.

8. A system comprising:

one or more data processors; and a non-transitory computer readable storage medium containing instructions which when executed on the one or more data processors, cause the one or more data processors to perform actions including:

availing a graph model, wherein the graph model includes a graph structure that connects a set of nodes and a set of edges, each edge of the set of edges connecting two nodes, the set of nodes including a plurality of end nodes, each end node of the plurality of end nodes identifying a clinical investigatory event;

for each entity of a set of entities:

identifying a starting node from amongst the set of nodes based on first electronic data associated with the entity;

generating one or more graph-structure trajectories through part of the graph structure based on second electronic data associated with the entity, each graph-structure trajectory of the one or more graph-structure trajectories extending from the starting node through one or more edges and connecting to one or more other nodes of the set of nodes, wherein generating the one or more graph-structure trajectories includes iteratively determining, for each graph-structure trajectory of the one or more trajectories, whether to extend the graph-structure trajectory to a next node in a path based on at least part of the second electronic data and a criteria group of the next node until the graph-structure trajectory terminates; and storing graph-structure trajectory data characterizing each of the one or more graph-structure trajectories in association with an identifier of the entity;

identifying a parent node connected to a plurality of child nodes via a corresponding edge, each of the plurality of child nodes being associated with a corresponding clinical-trial-participation criterion that is more specific than a clinical-trial-participation criterion associated with the parent node;

identifying a subset of the set of entities based on the stored graph-structure trajectory data, wherein graph-model trajectory data for each entity in the subset indicates that a graph-structure trajectory associated with the entity connected to a child node of the plurality of child nodes and that the clinical-trial-participation criterion associated with the parent node is satisfied with respect to the entity;

retrieving investigatory-event data associated with the subset of the set of entities, wherein the investigatory-event data includes information indicative of one or more results corresponding to multiple clinical investigatory events corresponding to multiple end nodes, wherein, for each entity in the subset of the set of entities, a graph-structure trajectory of the one or more graph-structure trajectories associated with the entity connects the child node to an end node of the multiple end nodes, the plurality of end nodes including the multiple end nodes;

generating, based on the investigatory-event data, a data-integration result, wherein the data-integration result is generated to correspond with the clinical-trial-participation criterion associated with the parent node; and outputting the data-integration result.

9. The system as recited in claim 8, wherein the iterative determination of whether to extend the graph-structure trajectory includes determining to terminate the graph-structure trajectory when the trajectory has reached an end node of the plurality of end nodes or when a result of an assessment of the criteria group using the at least part of the second electronic data indicates that:
if the criteria group is an inclusion criteria group, the criteria group is not satisfied; or
if the criteria group is an exclusion criteria group, the criteria group is satisfied.

10. The system as recited in claim 8, wherein:
the clinical-trial-participation criterion associated with the parent node indicates a first type of condition;
the corresponding clinical-trial-participation criterion associated with each of the plurality of child nodes indicates a corresponding second type of condition; and
each of the corresponding second type of condition is a sub-type of the first type of condition;
each of the plurality of child nodes includes an end node identifying a corresponding clinical investigatory event that involves investigating a particular type of treatment, the particular type of treatment being the same across the plurality of child nodes; and
the data-integration result includes a result of treating the first type of condition with the particular type of treatment.

11. The system as recited in claim 8, wherein:
each of the plurality of child nodes includes an end node;
the corresponding clinical-trial-participation criterion associated with each of the plurality of child nodes indicates a type of treatment provided during the clinical investigatory event identified by the child node, the indicated types of treatment being different across the plurality of child nodes but corresponding to a particular treatment class that is the same across the plurality of child nodes;
the clinical-trial-participation criterion associated with the parent node indicates the particular treatment class;
for each child node of the plurality of child nodes, the clinical investigatory event identified by the child node corresponds to a particular type of disease that is the same across the plurality of child nodes; and
the data-integration result includes a result of treating the particular type of disease with the particular treatment class.

12. The system as recited in claim 8, wherein the data-integration result includes one or more weights or one or more coefficients, wherein each of the one or more weights or one or more coefficients indicates a degree to which a corresponding entity attribute statistically relates to an investigatory-event outcome.

13. The system as recited in claim 12, wherein the investigatory-event outcome characterizes an efficacy of a treatment and/or a prevalence of one or more types of adverse effects to the treatment.

14. The system as recited in claim 8, wherein identifying the parent node includes:
determining that the corresponding clinical-trial-participation criterions associated with the plurality of child nodes are related; and
generating the parent node and generating a set of new edges to connect the parent node to the plurality of child nodes.

15. The system as recited in claim 8, wherein:
each of the plurality of child nodes includes an end node;
for a first child node of the plurality of child nodes, the corresponding clinical-trial-participation criterion associated with the first child node includes a first value that conforms with a first controlled vocabulary; and
for a second child node of the plurality of child nodes, the corresponding clinical-trial-participation criterion associated with the second child node includes a second value that conforms with a second controlled vocabulary, the first controlled vocabulary being different than the second controlled vocabulary, and the first value and second value representing a similar or same condition or treatment.

16. A computer-program product tangibly embodied in a non-transitory machine-readable storage medium, including instructions configured to cause one or more data processors to perform actions including:
availing a graph model, wherein the graph model includes a graph structure that connects a set of nodes and a set of edges, each edge of the set of edges connecting two nodes, the set of nodes including a plurality of end nodes, each end node of the plurality of end nodes identifying a clinical investigatory event;
for each entity of a set of entities:
identifying a starting node from amongst the set of nodes based on first electronic data associated with the entity;
generating one or more graph-structure trajectories through part of the graph structure based on second electronic data associated with the entity, each graph-structure trajectory of the one or more graph-structure trajectories extending from the starting node through one or more edges and connecting to one or more other nodes of the set of nodes, wherein generating the one or more graph-structure trajectories includes iteratively determining, for each graph-structure trajectory of the one or more trajectories, whether to extend the graph-structure trajectory to a next node in a path based on at least part of the second electronic data and a criteria group of the next node until the graph-structure trajectory terminates; and
storing graph-structure trajectory data characterizing each of the one or more graph-structure trajectories in association with an identifier of the entity;
identifying a parent node connected to a plurality of child nodes via a corresponding edge, each of the plurality of child nodes being associated with a corresponding clinical-trial-participation criterion that is more specific than a clinical-trial-participation criterion associated with the parent node;
identifying a subset of the set of entities based on the stored graph-structure trajectory data, wherein graph-model trajectory data for each entity in the subset indicates that a graph-structure trajectory associated with the entity connected to a child node of the plurality of child nodes and that the clinical-trial-participation criterion associated with the parent node is satisfied with respect to the entity;
retrieving investigatory-event data associated with the subset of the set of entities wherein the investigatory-event data includes information indicative of one or more results corresponding to multiple clinical investigatory events corresponding to multiple end nodes, wherein, for each entity in the subset of the set of entities, a graph-structure trajectory of the one or more graph-structure trajectories associated with the entity connects the child node to an end node of the multiple end nodes, the plurality of end nodes including the multiple end nodes;

generating, based on the investigatory-event data, a data-integration result, wherein the data-integration result is generated to correspond with the clinical-trial-participation criterion associated with the parent node; and outputting the data-integration result.

17. The computer-program product as recited in claim 16, wherein the iterative determination of whether to extend the graph-structure trajectory includes determining to terminate the graph-structure trajectory when the trajectory has reached an end node of the plurality of end nodes or when a result of an assessment of the criteria group using the at least part of the second electronic data indicates that:

if the criteria group is an inclusion criteria group, the criteria group is not satisfied; or if the criteria group is an exclusion criteria group, the criteria group is satisfied.

18. The computer-program product as recited in claim 16, wherein:

the clinical-trial-participation criterion associated with the parent node indicates a first type of condition;

the corresponding clinical-trial-participation criterion associated with each of the plurality of child nodes indicates a corresponding second type of condition; and each of the corresponding second type of condition is a sub-type of the first type of condition;

each of the plurality of child nodes includes an end node identifying a corresponding clinical investigatory event that involves investigating a particular type of treatment, the particular type of treatment being the same across the plurality of child nodes; and the data-integration result includes a result of treating the first type of condition with the particular type of treatment.

19. The computer-program product as recited in claim 16, wherein:

each of the plurality of child nodes includes an end node;

the corresponding clinical-trial-participation criterion associated with each of the plurality of child nodes indicates a type of treatment provided during the clinical investigatory event identified by the child node, the indicated types of treatment being different across the plurality of child nodes but corresponding to a particular treatment class that is the same across the plurality of child nodes;

the clinical-trial-participation criterion associated with the parent node indicates the particular treatment class;

for each child node of the plurality of child nodes, the clinical investigatory event identified by the child node corresponds to a particular type of disease that is the same across the plurality of child nodes; and the data-integration result includes a result of treating the particular type of disease with the particular treatment class.

20. The computer-program product as recited in claim 16, wherein the data-integration result includes one or more weights or one or more coefficients, wherein each of the one or more weights or one or more coefficients indicates a degree to which a corresponding entity attribute statistically relates to an investigatory-event outcome.

* * * * *